(12) United States Patent
Corr et al.

(10) Patent No.: US 7,084,315 B2
(45) Date of Patent: Aug. 1, 2006

(54) REMOVAL OF (HYDRO)HALOALKENE IMPURITIES FROM PRODUCT STREAMS

(75) Inventors: Stuart Corr, Warrington (GB); John Charles McCarthy, Warrington (GB)

(73) Assignee: Ineos Fluor Holdings Limited (GB)

( * ) Notice: Subject to any disclaimer, the term of this patent is extended or adjusted under 35 U.S.C. 154(b) by 332 days.

(21) Appl. No.: 10/258,998

(22) PCT Filed: May 2, 2001

(86) PCT No.: PCT/GB01/01920

§ 371 (c)(1),
(2), (4) Date: Feb. 18, 2003

(87) PCT Pub. No.: WO01/83411

PCT Pub. Date: Nov. 8, 2001

(65) Prior Publication Data

US 2003/0157009 A1    Aug. 21, 2003

(30) Foreign Application Priority Data

May 4, 2000  (GB) ................. 0010614.6

(51) Int. Cl.
*C07C 17/38* (2006.01)
(52) U.S. Cl. ...................... 570/177; 570/179
(58) Field of Classification Search ........... 570/177, 570/179
See application file for complete search history.

(56) References Cited

U.S. PATENT DOCUMENTS

| | | | |
|---|---|---|---|
| 3,215,747 | A | 11/1965 | Fainberg et al. |
| 3,804,910 | A | 4/1974 | Furrow |
| 4,129,603 | A | 12/1978 | Bell |
| 4,906,796 | A | 3/1990 | Yates |
| 5,233,107 | A | 8/1993 | Jansen |

FOREIGN PATENT DOCUMENTS

| | | |
|---|---|---|
| CA | 2004709 | 9/1990 |
| EP | 0389334 A | 9/1990 |
| JP | 1-207497 | 8/1989 |
| JP | 3-72437 | 3/1991 |
| JP | 03 072437 | 3/1991 |
| WO | PCT/GB01/01920 | 5/2000 |
| WO | PCT/GB01/01920 | 5/2001 |
| WO | PCT/GB01/01920 | 11/2001 |

*Primary Examiner*—Sikarl A. Witherspoon
(74) *Attorney, Agent, or Firm*—Cook, Alex, McFarron, Manzo, Cummings & Mehler, Ltd.

(57) ABSTRACT

A process for removing a (hydro)haloalkene impurity from a product stream containing that impurity and a desired compound is described. The process comprises contacting the product stream with a solid adsorbent comprising pores having openings which have a size across their largest dimension in the range of from about 7 Å to about 10 Å. The process is particularly suited to the removal of (hydro) halopropene impurities from saturated hydrofluorocarbons such as a tetrafluoroethane, a pentafluoropropane, a hexafluoropropane or a heptafluoropropane.

18 Claims, No Drawings

REMOVAL OF (HYDRO)HALOALKENE IMPURITIES FROM PRODUCT STREAMS

This application is a national stage application based upon International Application No. PCT/GB01/01920, filed May 2, 2001, which is based upon Great Britain Priority Patent Application No. 0010614.6, filed May 4, 2000, the priority of which is hereby claimed under 35 USC §119.

This invention relates to a process for removing (hydro) haloalkene impurities from a product stream containing a desired compound. More particularly, the present invention relates to the removal of (hydro)haloalkene impurities, and especially (hydro)halopropene impurities, from a saturated hydrofluorocarbon such as a tetrafluoroethane, a pentafluoropropane, a hexafluoropropane or a heptafluoropropane.

Chlorofluorocarbons have found widespread use as refrigerants, foam blowing agents, aerosol propellants and cleaning solvents. However, these materials have been implicated in the destruction of the earth's protective ozone layer and their use is now controlled under the Montreal Protocol.

Hydrofluorocarbons are currently of interest as replacements for fully and partially halogenated chlorofluorocarbons. For example, the refrigerant dichlorodifluoromethane (R-12) is generally being replaced by 1,1,1,2-tetrafluoroethane (R-134a).

Various processes are available for the manufacture of hydrofluorocarbons. In one known process, the hydrofluorocarbon is prepared by reacting a chlorofluorocarbon with hydrogen fluoride or an alkali metal fluoride in the vapour phase. Catalysts or electrochemical means are generally used to facilitate this reaction. This process often generates a number of by-products, the nature and quantity of which depend on a number of factors.

For example, 1,1,1,2-tetrafluoroethane can be prepared by the reaction of 1-chloro-2,2,2-trifluoroethane with hydrogen fluoride in the vapour phase in the presence of a chromium containing catalyst. This process may be carried out under atmospheric or super atmospheric pressure at a temperature of from 250° C. to 500° C.

Other known methods for preparing R-134a include: fluorination of 1-chloro-2,2,2-trifluoroethane; hydrofluorination of trifluoroethylene and hydrogenation of 2,2-dichloro-1,1,1,2-tetrafluoroethane or 2-chloro-1,1,1,2-tetrafluoroethane.

Processes for the production of hydrofluorocarbons such as R-134a may result in product streams which are contaminated with (hydro)haloalkene impurities such as 1-chloro-2,2-difluoroethylene (R-1122), 2,3,3,3-tetrafluoropropene (R-1234yf), 3,3,3-trifluoropropene (R-1243zf), perfluoropropene (R-1216), 1,1,3,3,3-pentafluoropropene (R-1225zc) and 2-chloro-1,1,3,3,3-pentafluoropropene (R-1215xc).

The presence of small quantities of impurities is not detrimental to the bulk physical properties of the hydrofluorocarbon product and for many applications their removal is unnecessary. However, some of the potential applications for hydrofluorocarbons, such as their use as a propellant for pharmaceuticals, as solvents in the food industry or for plasma cleaning and etching, require very low levels of impurities and particularly unsaturated impurities such as R-1234yf, R-1243zf and R-1122.

Impurities are often removed by distillation, but this method of removal is made difficult if the boiling point of the impurity is close to that of the desired product. Furthermore, even after distillation, it is possible that small quantities of undesirable impurities will remain. Thus, the method of removing unsaturated hydrohalocarbon impurities from hydrofluorocarbon products by distillation is not always satisfactory and there is a need for an alternative purification method.

A number of alternative methods of purifying hydrofluorocarbon products have been previously proposed.

U.S. Pat. No. 4,129,603 discloses a method of removing 1-chloro-2,2-difluoroethylene from 1,1,1,2-tetrafluoroethane. The method comprises contacting the mixture with an aqueous solution of potassium permanganate.

U.S. Pat. No. 4,906,796 discloses a method for the removal of 1-chloro-2,2-difluoroethylene from 1,1,1,2-tetrafluoroethane. The method comprises passing the mixture over a zeolite having a mean pore size of from 3.8 to 4.8 Å at a temperature of from −10° C. to 100° C. and a pressure of from 100 to 860 kPa. The preferred zeolites are 5 Å synthetic zeolite or calcium chabazite. The removal of 1-chloro-2,2-difluoroethylene by this method is highly selective and other impurities in the mixture are substantially unaffected.

JP-1-207497 also discloses a method for the removal of fluoroalkenes and chlorofluorocarbons from 1,1,1,2-tetrafluoroethane comprising passing the mixture over a zeolite. The preferred zeolites have pore diameters of from 5 to 7 Å. However, the process is only successful when the 1,1,1,2-tetrafluoroethane raw material has a purity of at least 99% by weight and so distillation is generally required before the mixture is contacted with the zeolite.

None of the prior art documents discussed above disclose an effective method for removing (hydro)halopropene by-products which may contaminate the product streams which are produced in the known processes for preparing hydrofluorocarbons. Thus, there is a need for a process which is able to remove the (hydro)halopropene by-products contaminating a hydrofluorocarbon containing product stream. Furthermore, none of the documents recognise the utility of adsorbents having a pore size of greater than 7 Å for removing (hydro)haloalkenes.

It has now been found that (hydro)haloalkene and particularly (hydro)halopropene impurities can be removed from a product stream containing a desired product, such as a saturated hydrofluorocarbon, by contacting the product stream with a solid adsorbent, such as a zeolite molecular sieve, comprising pores of a particular dimension.

According to the present invention there is provided a process for removing at least one (hydro)haloalkene, particularly (hydro)halopropene impurity from a product stream containing that impurity and at least one desired compound, which process comprises contacting the product stream with a solid adsorbent comprising pores having openings which have a size across their largest dimension in the range of from about 7 Å to about 10 Å, e.g. from greater than 7 Å to less than 10 Å.

In the process of the present invention, the (hydro) haloalkene, e.g. (hydro)halopropene impurity is adsorbed by the adsorbent and is retained within its porous structure while the purified product stream containing the desired compound passes through the adsorbent and is subsequently recovered. By the term "(hydro)haloalkene" we are referring to unsaturated compounds that contain halogen and optionally hydrogen atoms in addition to carbon atoms. Thus, the term includes perhaloalkenes as well as hydrohaloalkenes that contain both hydrogen and halogen atoms in addition to the carbon atoms. In referring to halogen atoms, we are particularly referring to fluorine and/or chlorine atoms. The same definition applies to the term "(hydro)halopropenes".

The process of the present invention is particularly suited to removing (hydro)haloalkene and especially (hydro)halopropene impurities from a product stream comprising a saturated hydrofluorocarbon product. By the term "hydrofluorocarbon" we mean compounds that contain only carbon, hydrogen and fluorine atoms in their structure.

Accordingly, in a preferred embodiment the present invention provides a process for removing at least one (hydro)haloalkene, particularly (hydro)halopropene impurity from a product stream containing that impurity and at least one hydrofluorocarbon, which process comprises contacting the product stream with a solid adsorbent comprising pores having openings which have a size across their largest dimension in the range of from about 7 Å to about 10 Å.

Suitable saturated hydrofluorocarbons include the hydrofluoroethanes and the hydrofluoropropanes, with the tetrafluoroethanes, pentafluoropropanes, hexafluoropropanes and heptafluoropropanes being preferred. In a particularly preferred embodiment, the process of the present invention is concerned with the removal of one or more hydrohalopropene impurities from a product stream comprising 1,1,1,2-tetrafluoroethane (R-134a), 1,1,1,2,3,3,3-heptafluoropropane (R-227ea), 1,1,1,2,3,3-hexafluoropropane (R-236ea), 1,1,1,2,2,3-hexafluoropropane (R-236cb), 1,1,1,3,3,3-hexafluoropropane (R-236fa), 1,1,2,2,3-pentafluoropropane (R-245ca) or 1,1,1,3,3-pentafluoropropane (R-245fa), especially R-134a and R-227ea.

Of course, the hydrofluorocarbon containing product stream may contain other impurities in addition to the (hydro)haloalkenes, such as saturated hydrochlorofluorocarbons.

The present invention can be used to remove various (hydro)haloalkene impurities which contaminate product streams.

The (hydro)halopropene impurities which the present invention is particularly concerned with removing are R-1234yf, R-1243zf, perfluoropropene (R-1216), 1,1,3,3,3-pentafluoropropene (R-1225zc) and 2-chloro-1,1,3,3,3-pentafluoropropene (R-1215xc).

The hydrofluoropropenes R-1234yf and R-1243zf can be produced as by-products in the known processes for manufacturing R-134a. Accordingly, in one preferred embodiment, the present invention is concerned with the removal of R-1234yf and R-1243zf which contaminate a R-134a containing product stream.

The (hydro)fluoropropenes R-1216, R-1225zc and R-1215xc can be produced as by-products in the manufacture of R-227ea. Accordingly, in another preferred embodiment, the present invention is concerned with the removal of R-1216, R-1225zc and R-1215xc which contaminate a R-227ea containing product stream.

The present invention may also be used to remove any R-1122 contaminating product streams. This unsaturated alkene can also be produced as a by-product in the known processes for manufacturing R-134a.

As stated above, the present invention is particularly directed to the removal of (hydro)halopropene impurities which contaminate product streams. However, even in this preferred embodiment the solid adsorbent which is used in the process may remove other (hydro)haloalkenes which contaminate the product stream in addition to the (hydro)halopropenes. For example, in the manufacture of R-134a, R-1122 may also be produced as a by-product, and it has been found that the present process can remove R-1122 and (hydro)halopropenes simultaneously. Additionally, the manufacture of R-227ea may result in the production of a hydrohalobutene or perhalobutene by-product in addition to the (hydro)halopropenes, and the present process may also be capable of effecting removal of these compounds simultaneously. Thus, even this preferred embodiment of the present process is not limited to the sole removal of (hydro)halopropenes.

The adsorbent which is used in the process of the present invention contains pores having openings which have a size across their largest dimension in the range of from about 7 Å to about 10 Å, e.g. from greater than 7 Å to less than 10 Å. By opening we are referring to the mouth of the pore by which the (hydro)haloalkene enters the body of the pore where it becomes trapped. The openings to the pores may be elliptically shaped, essentially circular or even irregularly shaped, but will generally be elliptically shaped or essentially circular. When the pore openings are essentially circular, they should have a diameter in the range of from about 7 Å to about 10 Å, e.g. from greater than 7 Å to less than 10 Å.

When the adsorbent has pores having elliptically shaped openings which are below 7 Å across their smallest dimension, it can still be effective at adsorbing (hydro)halopropenes providing that the size of the openings across their largest dimension is in the range of from about 7 Å to about 10 Å and preferably greater than 7 Å to less than 10 Å.

Preferred adsorbents are those comprising pores having openings which have a size across their largest dimension in the range of from greater than 7 Å to 9 Å, more preferably in the range of from greater than 7 Å to 8 Å.

The adsorbent which is used in the present process is preferably a molecular sieve and more preferably is a carbon or zeolite molecular sieve. In a particularly preferred embodiment, the adsorbent is a zeolite molecular sieve.

Particularly preferred zeolites are zeolite-Beta and zeolite-Y. Zeolite-Beta contains pores having predominantly elliptical openings some of which have a size across their largest and smallest dimensions of 7.6 Å and 6.4 Å respectively. Zeolite Y contains pores having circular openings of 7.4 Å in diameter.

The performance of zeolite Beta and zeolite Y can be altered by changing the nature of the cations contained in the zeolite. A variety of cations can be contained in the zeolite without affecting its ability to adsorb (hydro)haloalkenes. Preferably, the cations contained in the zeolite are selected from hydrogen, potassium, sodium and calcium and more preferably are hydrogen, potassium or sodium, especially hydrogen. Zeolite-Beta-Na, zeolite-Beta-H and zeolite-Y-H are particularly effective at selectively removing both R-1234yf and R-1243zf from 1,1,1,2-tetrafluoroethane. These zeolite molecular sieves can also significantly reduce the levels of R-1122 in a R-134a containing product stream.

If the adsorbent only contains pores having openings which have a size across their largest dimension of greater than 10 Å, the ability of the adsorbent to adsorb (hydro)halopropenes is lost. Thus, there is a relatively narrow range of adsorbent pore sizes that provide for effective adsorption of (hydro)halopropenes.

The adsorbent may contain more than one distribution of pore sizes, so that in addition to the pores of the required dimension in which the openings to the pores have a size across their largest dimension in the range of from 7 Å to 10 Å, the adsorbent may also contain pores which are either larger or smaller. Thus, the adsorbent does not have to contain exclusively pores within the 7 Å to 10 Å range. However, any pores outside this range will not be effective at removing (hydro)halopropenes.

It has also been found that zeolite molecular sieves that are useful in the present invention tend to be poor at adsorbing saturated hydrohalocarbon impurities present in the mixture. For example, 1,1,2,2-tetrafluoroethane (R-134), which is often produced as a by-product in the manufacture of R-134a, is not significantly adsorbed by the zeolite molecular sieves. This is advantageous in that the zeolite retains the ability to adsorb the unsaturated impurities in the presence of relatively large quantities of saturated impurities.

The adsorbent should be in particulate form and is conveniently in the form of pellets. The particulate adsorbent is typically arranged as a bed or layer in an adsorption tower or column and the product stream may be conveyed over or through the bed. The adsorbent bed may be a fluidised or moving bed, but in a preferred embodiment is a fixed or static bed.

The adsorbent typically has a surface area in the range of from 300 to 900 m$^2$/g.

The adsorbent is normally pre-treated prior to use by heating in a dry gas stream, such as dry air or dry nitrogen. This process is known to those skilled in the art and has the effect of activating the adsorbent. Typical temperatures for the pre-treatment are in the range of from 100 to 400° C.

The process of the present invention can be conducted with the product stream in the liquid phase or the vapour phase. Typically, the product stream exiting the reactor will be pre-treated before it is subjected to the process of the present invention in order to reduce the overall level of impurities in the product stream. This pre-treatment will typically include a distillation step. The product stream may also be re-circulated and conducted several times through the same adsorbent bed in order to achieve the desired low level of unsaturated impurities.

The process of the invention may be operated in a batch or continuous manner although continuous operation is preferred.

The present process is preferably operated at a temperature in the range of from −20 to 100° C., more preferably in the range of from 10 to 70° C. and particularly in the range of from 20 to 50° C.

The preferred operating pressures are in the range of from 1 to 30 bar, more preferably in the range of from 5 to 20 bar and particularly in the range of from 6 to 12 bar.

The preferred feed rate for the product stream to the adsorbent bed is in the range of from 0.1 to 50 hour$^{-1}$, more preferably in the range of from 1 to 30 hour$^{-1}$ for liquid phase product streams and in the range of from 10 to 10,000 hour$^{-1}$, more preferably in the range of from 100 to 5000 hour$^{-1}$ for vapour phase product streams.

The level of (hydro)haloalkenes contaminating the product stream which is subjected to the process of the present invention is typically in the range of from 0.1 to 100 parts per million (ppm) by weight, more typically in the range of from 0.1 to 20 ppm by weight, e.g. 0.1 to 10 ppm by weight. Following purification by the process of the present invention, the level of (hydro)haloalkenes contaminating the product stream will typically be in the range of from 0.01 to 5 ppm by weight, preferably in the range of from 0.01 to 2 ppm by weight and particularly in the range of from 0.01 to 1 ppm by weight.

During operation of the present process, the adsorption capability of the adsorbent is gradually consumed as the pores become occupied with the unsaturated impurities. Eventually, the ability of the adsorbent to adsorb the unsaturated impurities will be substantially impaired and at this stage the adsorbent must be regenerated. Regeneration is typically effected by heating the used adsorbent in a dry gas stream, such as dry air or dry nitrogen, at a temperature in the range of from 100 to 300° C., e.g. 100 to 200° C., and a pressure in the range of from 1 to 30 bar, e.g. 5 to 15 bar. This process is known to those skilled in the art.

The present invention is now illustrated but not limited by the following example.

EXAMPLE 1

A range of zeolite molecular sieves were obtained as follows:
1. Zeolite Beta (hydrogen form; Zeolyst International). Contains elliptically shaped pores having a size of 7.4×6.4 Å as well as circular pores of 5.5 Å diameter.
2. Zeolite Y (hydrogen form; Zeolyst International). Contains circular pores of 7.4 Å diameter.
3. Zeolite ZSM5 (hydrogen form; Zeolyst International). Contains approximately circularly shaped pores of size 5.3×5.6 Å.
4. Mordenite (sodium form; Zeolyst International). Contains elliptically shaped pores having a size of 6.5×7.0 Å.
5. Zeolite MS-13X (Grace Davison). Nominal pore diameter 10 Å.
6. Zeolite MS-5A (Grace Davison). Pore size 4.2 Å.
7. Zeolite AW500. Pore size 3.7 to 4.2 Å.

Some of the zeolites were ion exchanged to replace the cations. This was accomplished by repeated washing of the zeolite with aliquots of dilute (0.1 M) solutions of the respective metal chloride salts, followed by repeated washing with deionised water at room temperature. The zeolites were then dried by heating to 300° C. in a stream of dry nitrogen (200 ml/min) for a period of 18 hours.

Samples of R-134a containing a range of impurities were analysed by gas chromatography. Weighed liquid aliquots of the impure R-134a samples were then placed in contact with weighed samples of the zeolite adsorbents (in extruded pellet form) in sealed, stainless steel bombs. The liquid mixtures were stored at room temperature for a period of 24 hours in order to reach equilibrium. After this time, the liquid R-134a was removed for duplicate analysis by gas chromatography and the results compared to the original R-134a sample. The results of the analyses pre- and post-treatment with the various zeolites are given in Tables 1 and 2.

TABLE 1

| Zeolite | R-134a:Zeolite Ratio | R-134 (ppm w/w) | R-1122 (ppm w/w) | R-1234yf (ppm w/w) | R-1243zf (ppm w/w) | R-1122a (ppm w/w) |
|---|---|---|---|---|---|---|
| Pre-treatment | N/a | 995.9 | 7.4 | 2.9 | 2.6 | 5.2 |
| MS-13X | 14.99 | 700.9 | 6.9 | 3.0 | 2.5 | 5.4 |
| AW500 | 14.19 | 107.7 | 0.0 | 3.0 | 1.2 | 1.7 |
| MS-5A | 11.02 | 380.4 | 2.5 | 2.9 | 2.7 | 2.3 |
| Mordenite-Na | 14.35 | 896.6 | 4.1 | 2.7 | 1.3 | 3.7 |

TABLE 2

| Zeolite | R-134a: Zeolite Ratio | R-134 (ppm w/w) | R-1122 (ppm w/w) | R-1234yf (ppm w/w) | R-1243zf (ppm w/w) | R-1122a (ppm w/w) |
|---|---|---|---|---|---|---|
| None | N/a | 1030.2 | 7.6 | 1.5 | 1.5 | 4.1 |
| Beta-H | 20.77 | 1073.1 | 6.9 | 0.0 | 0.0 | 3.3 |
| Beta-Na | 16.44 | 1143.5 | 5.3 | 0.0 | 0.0 | 2.3 |
| Beta-Ca | 12.90 | 971.9 | 6.5 | 0.5 | 0.0 | 3.0 |
| ZSM5-H | 16.09 | 1017.1 | 4.8 | 1.8 | 0.0 | 2.8 |
| Y-H | 9.88 | 998.3 | 2.8 | 0.0 | 0.0 | 3.0 |
| Y-Ca | 10.22 | 1061.4 | 2.2 | 0.9 | 0.0 | 3.4 |

The results clearly show that zeolite-Beta and zeolite-Y are capable of completely removing both R-1234yf and R-1243zf from 1,1,1,2-tetrafluoroethane. Zeolite-beta-H, zeolite-beta-Na and zeolite-Y-H are the most effective at removing both R-1234yf and R-1243zf from 1,1,1,2-tetrafluoroethane. Zeolites with both larger and smaller pore sizes than zeolite-Beta and zeolite-Y are ineffective at reducing the levels of both R-1234yf and R-1243zf. Zeolite-beta-Ca, zeolite-ZSM5-H and zeolite-Y-Ca are capable of reducing levels of R-1243zf alone.

Thus, the experimental results show that only zeolites with pores having openings which have a size across their largest dimension in the range of from 7 Å to 10 Å are capable of adsorbing a significant proportion of the unsaturated hydrohalopropene impurities.

The results also show that zeolite-Y is capable of removing appreciable quantities of R-1122 from 1,1,1,2-tetrafluoroethane.

The invention claimed is:

1. A process for removing at least one (hydro)haloalkene impurity that comprises at least one (hydro)halopropene from a product stream containing that impurity and at least one desired compound, which process is conducted at a temperature of from −20° C. to 100° C. and comprises adsorbing the impurity by contacting the product stream with a solid adsorbent comprising pores having openings which have a size across their largest dimension in the range of from greater than 7 Å to about 10 Å.

2. A process as claimed in claim 1, wherein the at least one desired compound comprises at least one hydrofluorocarbon.

3. A process as claimed in claim 1, wherein the at least one (hydro)haloalkene impurity comprises at least one (hydro)halopropene and at least one other (hydro)haloalkene.

4. A process as claimed in claim 3, wherein the at least one other (hydro)haloalkene is 1-chloro-2,2-difluoroethylene.

5. A process as claimed in claim 1, wherein the at least one (hydro)halopropene comprises at least one of 2,3,3,3-tetrafluoropropene and 3,3,3-trifluoropropene.

6. A process as claimed in claim 5, wherein the product stream comprises 1,1,1,2-tetrafluoroethane.

7. A process as claimed in claim 1, wherein the at least one (hydro)halopropene comprises at least one compound selected from the group consisting of perfluoropropene, 1,1,3,3,3-pentafluoropropene and 2-chloro-1,1,3,3,3-pentafluoropropene.

8. A process as claimed in claim 7, wherein the product stream comprises 1,1,1,2,3,3,3-heptafluoropropane.

9. A process as claimed in claim 1, wherein the adsorbent comprises pores in which the openings to the pores have a size across their largest dimension in the range of from greater than 7 Å to less than 10 Å.

10. A process as claimed in claim 9, wherein the adsorbent comprises pores in which the openings to the pores have a size across their largest dimension in the range of from greater than 7 Å to 9 Å.

11. A process as claimed in claim 10, wherein the adsorbent comprises pores in which the openings to the pores have a size across their largest dimension in the range of from greater than 7 Å to 8 Å.

12. A process as claimed in claim 1, wherein the adsorbent is a molecular sieve.

13. A process as claimed in claim 1, wherein the adsorbent is a zeolite.

14. A process as claimed in claim 13, wherein the zeolite is selected from the group consisting of zeolite-Beta and zeolite-Y.

15. A process as claimed in claim 13, wherein the cations contained in the zeolite molecular sieve are selected from the group consisting of potassium, sodium, hydrogen and calcium.

16. A process as claimed in claim 1, wherein the adsorbent is an activated carbon.

17. A process for removing at least one (hydro)halopropene impurity that comprises 2,3,3,3,-tetrafluoropropene from a product stream containing that impurity and at least one desired compound, which process comprises adsorbing the impurity by contacting the product stream at a temperature of from −20 to 100° C. with a solid adsorbent comprising pores having openings which have a size across their largest dimension in the range of from about 7 Å to about 10 Å.

18. A process for removing at least one (hydro)halopropene impurity selected from the group consisting of perfluoropropene, 1,1,3,3,3-pentafluoropropene and 2-chloro-1,1,3,3,3-pentafluoropropene from a product stream containing that impurity and at least one desired compound, which process comprises adsorbing the impurity by contacting the product stream at a temperature of from −20 to 100°C. with a solid adsorbent comprising pores having openings which have a size across their largest dimension in the range of from about 7 Å to about 10 Å.

* * * * *